United States Patent
Winn

(10) Patent No.: US 8,993,641 B2
(45) Date of Patent: Mar. 31, 2015

(54) PRESERVATION OF COSMETICS, TOILETRY AND PHARMACEUTICAL COMPOSITIONS

(75) Inventor: Daniel Winn, Kingston, NJ (US)

(73) Assignee: Innolex Investment Corporation, Wilmington, DE (US)

(*) Notice: Subject to any disclaimer, the term of this patent is extended or adjusted under 35 U.S.C. 154(b) by 169 days.

(21) Appl. No.: 12/324,504

(22) Filed: Nov. 26, 2008

(65) Prior Publication Data

US 2009/0143489 A1    Jun. 4, 2009

Related U.S. Application Data

(60) Provisional application No. 61/004,760, filed on Nov. 29, 2007.

(51) Int. Cl.
| | |
|---|---|
| *A61K 47/16* | (2006.01) |
| *A61K 8/40* | (2006.01) |
| *A61Q 19/00* | (2006.01) |
| *A61Q 17/04* | (2006.01) |
| *A61K 8/34* | (2006.01) |

(52) U.S. Cl.
CPC ............. *A61K 47/16* (2013.01); *A61K 8/345* (2013.01); *A61K 8/40* (2013.01); *A61K 2800/524* (2013.01); *A61Q 17/04* (2013.01); *A61Q 19/00* (2013.01)
USPC ........................................ 514/785

(58) Field of Classification Search
CPC ..... A61K 8/345; A61K 31/047; A61K 31/16; A61K 47/16; A61K 8/40; A61K 2800/524; A61Q 17/04; A61Q 19/00
See application file for complete search history.

(56) References Cited

U.S. PATENT DOCUMENTS

| | | | |
|---|---|---|---|
| 3,632,764 A * | 1/1972 | Wakeman et al. | ............ 514/497 |
| 3,978,208 A | 8/1976 | Okada | |
| 4,256,765 A | 3/1981 | Munakata | |
| 4,661,342 A | 4/1987 | Yamazaki et al. | |
| 6,447,793 B2 | 9/2002 | Aust et al. | |
| 2005/0228032 A1 | 10/2005 | Merianos et al. | |
| 2006/0008434 A1 * | 1/2006 | Knopf et al. | ..................... 424/65 |
| 2007/0207105 A1 | 9/2007 | Winn | |

* cited by examiner

*Primary Examiner* — Renee Claytor
(74) *Attorney, Agent, or Firm* — Flaster/Greenberg P.C.

(57) ABSTRACT

A composition for and methods of preserving a topical cosmetic, toiletry or pharmaceutical formulation against microbiological contamination or growth are described in which the compositions used herein include at least one hydroxamic acid, salt or complex thereof, and the methods include addition of an effective amount of such compounds to a cosmetic, toiletry or pharmaceutical formulation. Compositions further including alkanediols and/or solubilizing agents in blends with hydroxamic acid are also described.

23 Claims, No Drawings

PRESERVATION OF COSMETICS, TOILETRY AND PHARMACEUTICAL COMPOSITIONS

CROSS REFERENCE TO RELATED APPLICATIONS

This application claims priority under 35 U.S.C. 119(e) to U.S. Provisional Patent Application 61/004,760, filed Nov. 29, 2007, the contents of which are incorporated herein by reference.

BACKGROUND OF THE INVENTION

Topical cosmetic, toiletry and pharmaceutical products such as creams, lotions, pastes, liquids, aerosols, shampoos, gels, wipes, bats, sticks, powders and granules, are known in the art to be susceptible to microbial infestation. The raw materials, packaging, and manufacturing environment for these products are often not sufficiently sterile, such that small amounts of microbiological contaminants can enter into final products. Shipment and storage of packaged cosmetic, toiletry and pharmaceutical products in some cases are performed under uncontrolled conditions. Often, a cosmetic, toiletry or pharmaceutical product may be exposed to higher temperatures than recommended which can also accelerate the growth rate of microbes unless a suitably effective antimicrobial component and/or components are incorporated into the formulation. Once product packages are opened, they are subject to further contamination from repeated consumer use. A consumer may notice microbial infestation by the discoloration and/or unpleasant odor of a product, or they might see macroscopic quantities of microorganisms such as mold on the product. Microbial growth can also cause the degradation of chemical and/or active compounds in the cosmetic, toiletry or pharmaceutical formulation, which can lead to instability of the product and/or emulsion. A product that has been contaminated by microbiological organisms can also lead to user infections once it is applied to the skin, scalp and/or mucous membranes of a human. It is therefore important for manufacturers and marketers of such products to be able to offer products that resist microbial growth and provide a stable and safe product with a long shelf life.

Typically, topical cosmetic, toiletry and pharmaceutical manufacturers add small amounts of one or more preservative compounds to their formulations to prevent microbial growth. The preferred preservatives may be water-soluble, since typically it is the water phase of a product that is most susceptible to microbial growth. The preferred preservatives are effective at use levels that lead to cost-effectiveness, and do not cause excessive irritation, a disadvantage that is associated with many preservative compounds. The preferred preservatives are those that do not adversely affect the aesthetic properties of the formulation such as the odor and the color. Furthermore, it is also desirable that the preservative does not affect the performance attributes and/or activity of the product. Finally, such preservatives must follow the guidelines established by individual national laws and regulations. In most countries, these regulations limit the type of and use-level of preservatives that may be included in a product. In some countries, certain preservatives are permitted only for rinse-off products (such as shower gels) but not for leave-on products (such as skin creams.) Therefore, preferred preservatives would be those that are not wholly prohibited in any country, and which are not restricted to only certain product types.

Preservatives used in topical cosmetic, toiletry and pharmaceutical products must also meet consumer preferences. In recent years, cosmetic preservatives have been a frequent target of academics and activist groups who question their toxicological safety. The resulting media reports have suggested that certain preservatives can be dangerous. As a result, manufacturers prefer to use preservatives not tainted by negative publicity and that will not adversely affect product marketability.

Preservatives used in cosmetic, toiletry and pharmaceutical products must enable the products to successfully pass microbiological testing protocols, known as "challenge tests", established by government regulations and trade organizations. Challenge tests are performed by adding known quantities of microorganisms to a product and measuring the increase or decrease in microorganism population over time. The organisms include Gram-positive bacteria, Gram-negative bacteria, yeast and mold. The Cosmetic, Toiletries, and Fragrance Association (CTFA) has defined a challenge test that is widely accepted as the standard in the cosmetic, toiletry and pharmaceutical industry. The test requires that the quantity of bacteria be reduced by 99% in seven days, and that the quantity of yeast and fungi (mold) be reduced by 90% in seven days. In order to pass a challenge test, the product must contain the appropriate amounts and types of preservative compounds that will enable antimicrobial efficacy against a broad spectrum of microorganisms in a short period of time.

In recent years cosmetic, toiletry and pharmaceutical manufacturers have been severely limited in their choice of preservative agents. One class of biocides that has been highly effective in cosmetic, toiletry and pharmaceutical products includes formaldehyde donors, such as imidazolidinyl urea, diazolidinyl urea, and DMDM hydantoin. However, many such compounds are considered to be skin irritants and the use of formaldehyde donors is severely restricted by regulations in the EU and Japan.

Another class of preservatives includes the isothiazolinones, such as KATHON® CG, available commercially from Rohm & Haas, Philadelphia, Pa., which contains a chloro-substituted isothiazolinone (methylchloroisothiazolinone). This chloro-substituted isothiazolinone has demonstrated irritation potential and it is prohibited from use in leave-on products in some countries.

Another class of preservatives is chlorinated aromatic compounds, such as chlorphenesin. They are not broadly used in cosmetic, toiletries or pharmaceuticals because they exhibit a very strong and unpleasant odor. Also chlorinated compounds in general are used in herbicides and pesticides, and many are known human toxins, and thus chlorinated compounds may have a negative consumer perception.

Yet another class of preservatives is para-hydroxybenzoic acids, known as parabens. Preservative blends containing parabens, such as GERMABEN® and LIQUAPAR®, available commercially from International Specialty Products, and PHENONIP®, available commercially from Clariant, are the most widely used preservative systems and have been used safely and effectively for over 20 years. However, research reports such as the recent Journal of Applied Toxicology [2004, 24, 5] have suggested that parabens are possible human carcinogens. The media has suggested that products containing parabens are dangerous. Consumer groups, such as Breast Cancer Action, have lobbied cosmetic and toiletry companies to remove parabens from their products. As a result parabens are now defacto banned from many segments of the cosmetic and toiletry industry.

In U.S. Published Patent Application US-2005-0228032-A1, International Specialty Products describes a paraben-free, broad-spectrum preservative blend that includes glycols, phenoxyethanol and organic acids. In U.S. Pat. No. 6,447,793 B2, Engelhard Corporation describes paraben-free, broad-spectrum preservation systems that include phenoxyethanol, chlorphenesin, and organic acids. Such blends fail to meet all of the industry-desired needs, because organic acids are only effective as biocides in products that have an acidic pH. Cosmetic, toiletry and pharmaceutical products having an acidic pH can be limited to certain leave-on formulations, such as creams and lotions. Organic acids are completely ineffective biocides at neutral pH, and thus these preservative blends are not suitable for pH-neutral cosmetic, toiletry and toiletry products, such as body washes and shampoos.

U.S. Patent Publication No. 2007-0207105-A1 describes an anti-microbial composition including a vicinal diol, which is a liquid at room temperature and an isothiazolinone compound to the composition. The vicinal diol may be a compound such as a 1,2-alkane diol or a glyceryl monoether. The isothiazolinone may be methylisothiazolinone, such as 2-Methyl-3(2H)isothiazolinone.

As referred to herein, compounds known as hydroxamic acids are part of a family of organic acids of general formula R—C(=O)—N(R')—OH. The alkenylhydroxamic acid, sorbic hydroxamic acid, is known in the art to have antifungal properties. See, e.g., W. F. Dudman, Appl. Microbiol., 11(4), pp. 362-364 (July, 1963). It has been proposed for use as a food preservative. However, sorbic hydroxamic acid is not used commercially for such an application because it has proven to be mutagenic. Alkylhydroxamic acids have excellent metal binding properties and their commercial use is almost entirely in the mineral processing industry for enhancing the recovery of valuable ores. See, e.g., Pradip and Fuerstenau, "Mineral Flotation with Hydroxamate Collectors", in "Reagents in the Minerals Industry", Ed. M. J. Jones and R. Oblatt, Inst. Min. Met., London, pp. 161-168 (1984). The commercial products AM2® from Ausmelt Limited of Melbourne, Australia, and AERO® S6493 from Cytec Industries, Inc., West Patterson, N.J., are mineral processing formulations containing alkylhydroxamic acids.

Alkylhydroxamic acids are also known to inhibit the catalytic activity of the enzyme urease, and therefore may be useful for reducing the odor that results from the decomposition of urine into ammonia. Esai Corporation Limited of Japan describes the use of alkylhydroxamic acids as part of deodorizing compositions as described in U.S. Pat. No. 3,978,208. Esai Corporation has also demonstrated that alkylhydroxamic acids may be useful for treating urinary kidney stones in humans as noted in U.S. Pat. No. 4,256,765. More recently, Lion Corporation of Japan demonstrated in U.S. Pat. No. 4,661,342 that saturated alkylhydroxamic acids, such as caprylohydroxamic acid, have anti-bacterial effectiveness against *Streptococcus mutans* in the human oral cavity. However, such compounds have not been adopted for topical cosmetic, toiletry and pharmaceutical formulations.

There is a need in the art for additional preservatives for topical cosmetic, toiletry and pharmaceutical purposes that are free of parabens, formaldehyde donors and chlorinated compounds, that are globally approved for use in leave-on and rinse-off products, and that have efficacy against a broad spectrum of microorganisms at various levels of pH, especially neutral pH.

BRIEF SUMMARY OF THE INVENTION

The present invention includes use of an effective amount at least one alkylhydroxamic acid, alone or in combination with at least one alcohol in topical cosmetic, toiletry and/or pharmaceutical preparations that are substantially free of parabens.

The invention includes a method of preserving a topical cosmetic, toiletry or pharmaceutical formulation against microbiological contamination or growth, comprising adding an effective amount of at least one hydroxamic acid, a salt and/or a complex thereof.

A composition is also within the scope of the invention herein which is useful for the preservation of topical cosmetic, toiletry and pharmaceutical formulations, wherein the composition is substantially free of parabens, comprising at least one hydroxamic acid, a salt and/or a complex thereof, and at least one alcohol.

Further included herein is a personal care product comprising a composition useful for the preservation thereof, wherein the composition is substantially free of parabens and comprises at least one hydroxamic acid, a salt and/or a complex thereof, and at least one alcohol.

Also within the scope hereof is a pharmaceutical product comprising a composition useful for the preservation thereof, wherein the composition is substantially free of parabens and comprises at least one hydroxamic acid, a salt and/or a complex thereof, and at least one alcohol.

DETAILED DESCRIPTION OF THE INVENTION

An alkylhydroxamic or hydroxamic acid as referred to herein may be present in its free (un-neutralized) or salt (neutralized) form, and it shall be understood that the terms "hydroxamic acid" and "alkylhydroxamic acid" include within the scope thereof the free acid form of the compounds as well as their salts and/or complexes thereof as well as materials which are precursors to such compounds, salts and complexes which upon addition react to form such compounds, salts and complexes, unless otherwise specifically noted.

The invention includes a method of preserving a substantially paraben free, topical, cosmetic, toiletry or pharmaceutical formulation against microbiological contamination or growth. As used herein, "topical" means application of the cosmetic, toiletry or pharmaceutical composition to the hair or skin and outer surfaces of the body, and does not include oral or other internal mucous membrane uses. The method includes adding an effective amount of at least one hydroxamic acid, salt, complex or precursor(s) thereof alone or in combination with an effective amount of at least one alcohol to such a formulation. Also within the invention is a preservative composition, substantially free of parabens, that includes a blend of at least one hydroxamic acid, salt, complex or precursor(s) thereof with at least one alcohol, as well as a personal care product or a pharmaceutical product including such preservative compositions.

In the method herein the at least one hydroxamic acid includes an alkylhydroxamic acid, such as those described further herein below. An alkylhydroxamic acid may have linear or branched carbon chain of from about two to about twenty-two carbon atoms, and preferably from about six to about twelve carbon atoms. The carbon chains may include double bonds, i.e., areas of unsaturation and may also have functionality depending on desired end use and properties. For example hydroxy groups may be beneficial side- or terminal-substituents on the chain leading to better water compatibility.

Other similar functional groups that meet the criteria of being compatible with and/or suggested for use in cosmetic, toiletry and/or pharmaceutical formulations are also within the scope of the invention. Such hydroxamic acids may also be synthesized from natural oils using lipase catalysis as well as other hydroxamic synthesis techniques known or to be developed in the art. Examples of such alkylhydroxamic acids include, but are not limited to hexanohydroxamic acid, caprylohydroxamic acid, caprohydroxamic acid, laurohydroxamic acid and mixtures and combinations thereof, and most preferably is caprylohydroxamic acid. It should be noted herein that precursors, such as hydroxy acids in combination with, for example, hydroxylamine hydrochloride or a similar compounds which can react within solution and/or in the formulation to form the various hydroxamic and alkylhydroxamic acids, salts and/or complexes thereof as are known in the art may also be used instead of a direct additive within the scope of the invention.

It is preferred that in the method, the composition further includes at least one alcohol, preferably a diol, and most preferably one or more vicinal diols. "Vicinal diols," as used herein, are materials that have hydroxyl groups which are bonded to atoms in the molecule which are next to each other, i.e., wherein two atoms each bearing a hydroxyl group are bonded to each other. Examples of vicinal diol compounds suitable for use in the invention, include, but are not limited to, ethylene glycol and propylene glycol. Such materials are known for use as humectants and solvents in cosmetic, toiletry and pharmaceutical products. They are also known to have some modest antimicrobial activity as described in U.S. Publication No. 2007-0207105-A1, the disclosure of which in relevant part related to vicinal diols, and compositions incorporating these compounds are incorporated herein by reference.

The most preferred vicinal diols for use in the compositions described herein when used in cosmetic, toiletry and pharmaceutical applications are medium-chain length, linear vicinal diols that demonstrate antimicrobial activity at relatively low use-levels. Such diols include 1,2-pentanediol, 1,2-hexanediol, caprylyl glycol, and 1,2-decanediol. Other vicinal diols useful in the compositions described herein include molecules derived from glycerin. Glycerin can be reacted with other molecules at its 1- or 3-position, leaving two vicinal hydroxyl groups. For example, glyceryl monoethers, such as ethylhexylglycerin[3-(2-ethylhexyloxy)propane-1,2-diol], available commercially as SENSIVA®SC50 from Schulke & Mayr, are useful liquid vicinal diols having antimicrobial properties. Glyceryl monoesters such as glyceryl monolaurate, glyceryl mono caproate, or glyceryl monocapyrlate, the latter of which is commercially available as LEXGARD® GMCY from Inolex Chemical Company, Philadelphia, Pa., are also useful antimicrobial vicinal diols. For the preservation of cosmetics, toiletries and pharmaceuticals, vicinal diols are known to be effective against bacteria and yeast but weak against fungi. In the book, D. Steinberg, Preservatives for Cosmetics. 2nd ed, (2006), pg. 102, the author comments regarding vicinal diols that "[t]he weakest activity on all of these is fungi." In the article, D. Smith et al., "The Self-Preserving Challenge," Cosmetic & Toiletries, No. 1, 115, No. 5 (May 2000), vicinal diols are described as having activity against bacteria, but to be "limited against *Aspergillus*." Since *Aspergillus niger* is one of the microorganisms used in the CTFA challenge test, products with vicinal diols as described herein as the only preservative may not sufficiently pass the CTFA challenge test.

The compositions described herein are useful for the preservation of topical cosmetic, toiletry and pharmaceutical formulations. In such formulations to achieve the benefits of the invention it is preferred that the compositions be substantially free of parabens, and preferably completely free of parabens. The compositions may be the same as those described above with respect to the method hereof.

The compositions preferably include at least one vicinal diol in amounts of, for example, about 0.001% by weight to about 99.999% by weight of the blend of the hydroxamic acid, salt or complex thereof with the at least one alcohol. The hydroxamic acid, salt or complex thereof preferably is present in an amount of about 0.001% to about 99.999% by weight of the noted blend. If precursors for hydroxamic acids, salts or complexes are used as components according to one aspect of the invention, the weight percentages described herein and further below, refer to the amount of formed compound desired in the blends in the compositions, wherein the compounds are formed from the precursor reaction or combination.

The compositions may further include a solubilizing agent in amounts of about 1% to about 70% by weight of the hydroxamic acid/alcohol blends. Examples of solubilizing agents include diols.

The invention also includes personal care products and pharmaceutical products that include compositions useful for the preservation thereof, wherein the compositions are also preferably substantially free of parabens and are as described herein according to the invention.

In personal care products, the compositions are preferably present in amounts of about 0.01 to about 10.00% by weight of the personal care product. In pharmaceutical products, the compositions are preferably present in an amount of from about 0.01 to about 10.00% by weight of the pharmaceutical product.

Despite these previous uses of hydroxamic acid in other industries, the invention describes a method including adding an effective amount of at least one alkylhydroxamic acid to topical cosmetic, toiletry and pharmaceutical formulations that result in a non-toxic, broad pH, and effective preservative method against a range of gram-positive bacteria, gram-negative bacteria, yeast and fungi. Formulations provided by the use of this method can pass regulatory acceptance criteria such as the CTFA challenge.

Suitable hydroxamic acids include alkylhydroxamic acids that include at least one alkyl group of a chain length of about two to about twenty-two carbon atoms, which may be branched or linear in structure, substituted or unsubstituted, and saturated or unsaturated as noted hereinabove. Preferred alkylhydroxamic acids contain alkyl groups of a chain length of about six to about twelve carbon atoms and most preferably linear chains of that length. Most preferred alkylhydroxamic acids are caprylohydroxamic acid, having a linear terminal chain of eight carbon atoms and caprohydroxamic acid, having a linear chain of ten carbon atoms. Such alkylhydroxamic acids may be used alone or in combination for varying effects and properties, and/or may be the result of use of precursors used as starting components as described above.

The preferred compounds have a formula as shown in Formula (I):

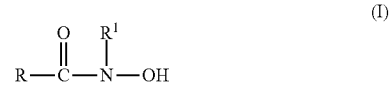

(I)

wherein R is a linear or branched, substituted or unsubstituted, carbon chain of about two to about twenty-two carbon atoms, which chain may be interrupted by one or more oxygen atoms, and may include saturated or unsaturated carbon bonds. Accordingly, R groups may include, for example, alkyl, alkenyl, alkynyl, alkoxy, alkenoxy, alkynoxy and similar groups, are branched or linear, and which groups may be further functionalized using substituted groups, including hydroxy or other acceptable cosmetic, toiletry and/or pharmaceutical end groups for use and compatible with such end applications. $R^1$ may be hydrogen or R.

Further effective preservation can be provided to the use of the hydroxamic acid if an effective amount of at least one alcohol is used in a blend with the at least one hydroxamic acid. The most preferred alcohols are vicinal diols.

In one preferred embodiment, caprylyl glycol is blended with caprylohydroxamic acid. In another preferred embodiment, caprylyl glycol is blended with caprylohydroxamic acid and further blended with one or more glycols or vicinal diols that are liquid at room temperature, such that the entire blend is liquid and therefore easy to blend into a cosmetic, toiletry or pharmaceutical emulsion. Such liquid glycols and vicinal diols include ethylhexylglycerin, 1,2-hexanediol, 1,2-pentanediol, propylene glycol, butylene glycol, and hexylene glycol.

It is preferred herein, that in preferred cosmetic, toiletry or pharmaceutical compositions, that the at least one hydroxamic acid is present in an amount of about 0.01 to about 10 percent by weight, and more preferably from about 0.1 to about 5 weight percent of a blend of the at least one alkylhydroxamic acid with the at least one vicinal diol and any optional solubilizing agent and/or water as noted herein. While only one alkylhydroxamic acid is necessary, such materials as described above may be used alone or in combinations with each other and with one or more vicinal diols. The amount of the alkylhydroxamic acid and the vicinal diol components in the blend should be selected so as to preferably provide a ratio of alkylhydroxamic acid(s) to vicinal diol(s) in the blend which is to be provided to the composition of about 99.999:0.001 to about 0.001:99.999 and more preferably about 10.00:0.01 to about 0.01:10.00, and most preferably about 10.0:0.1 to about 0.1:10.0.

In one preferred embodiment, an additional solvent is also incorporated into a blend of one vicinal diol and one alkylhydroxamic acid to make a blend of at least three components that is then incorporated into a cosmetic, toiletry or toiletry formulation. In such an embodiment, an additional glycol or vicinal diol that is liquid at room temperature is included in the blend in an amount of about 1 percent by weight to about 70 percent by weight of the blend, based on the total weight of the blend.

Formulations prepared for topical cosmetic and toiletry compositions herein referred to as personal care compositions, and topical pharmaceutical compositions, may include any other colorants, fragrances, active ingredients or other additives typically used and/or to be developed in the art for use in personal care and pharmaceutical formulations, in which additives will vary depending upon the formulation in which the preferred compositions are used, i.e., whether the formulations are used in skin treatments such as moisturizing compositions, skin toners, skin cleansers, night creams, skin creams, shaving creams, skin care lotions, or other cosmetic preparations; make-up, such as foundation, liquid and powder-based make-up, mascara, lipstick, blush, gloss, eye-liner and the like; or other personal care and/or pharmaceutical compositions, such as, sunscreens, lip balms, fragrances, massage oil, shampoos, conditioners, conditioning shampoos, hair styling gels, hair reparatives, hair tonics, hair fixatives, hair mousses, bath and shower gels, liquid soaps, moisturizing sprays, makeup, pressed powder formulations, bath additives, ophthalmic preparations, foaming soaps and body washes, sanitizing wipes, hand sanitizers, towelettes and wipes and others. It should be understood, based on this disclosure that a wide variety of personal care and pharmaceutical formulations could benefit from the properties of the methods and compositions of the present invention, wherein, as used herein, pharmaceutical product is a product including at least one active pharmaceutical ingredient (API).

The personal care and pharmaceutical formulations, if liquid based (such as gels, hydrogels, lotions, shampoos and the like) will also preferably include water as part of the liquid base. The formulations and compositions may include other additives as well, such as without limitation, at least one humectant, at least one emulsifier and/or thickener, chelating agent(s), gelling agent(s), amino acid(s), emollient(s), various solvents, free radicals and initiators, sunscreen UVA and/or UVB blocking agents, antioxidants, other preservatives, waxes, polymers and copolymers, inorganic and organic pigments and/or one or more fragrances, coloring agent(s), herbs, natural extracts, essential oils, pharmaceutical drug products, and other additives commonly used in such formulations.

The personal care and pharmaceutical compositions herein may be lotion-based, oil-in-water emulsions, water-in-oil emulsions, water-in-silicone emulsions, silicon-in-water emulsions, gels, solids, liquids, cream based, oil based, aqueous/alcoholic or glycolic solution based, dispersions, suspensions or syrups, microemulsions or a liposome-based formulations.

In water-based formulations, other than solids and thicker gels, etc., it is preferred that about 20% by weight to about 95% by weight (on a wet basis) of water is incorporated therein. The various additives aside from the water and preferred combination of preservatives noted herein including hydroxamic acids and alcohols, would make up the remaining portion of various personal care and pharmaceutical formulations based on the compositions described herein. Preferably, each additive is present in an amount of up to about 75 percent by weight of the entire formulation, and more preferably up to about 40 percent by weight, with a collective amount of such additives of preferably no greater than about 50 percent by weight.

Example 1

A skin care emulsion formulation was developed and then challenge tested. Table 1 describes two skin care formulations that are identical with the exception of their preservative system: Comparative Product A contains no preservative, while Product B contains 1.05% of a preservative blend according to the invention. The preservative blend in Product B is a combination of 95.2% caprylyl glycol and 4.8% caprylohydroxamic acid. The formulations are shown below in Table 1.

TABLE 1

|  | Comparative Formulation A (% w/w) | Formulation B (% w/w) |
| --- | --- | --- |
| Deionized Water | Q.S. | Q.S. |
| Xanthan Gum | 0.40 | 0.40 |
| Glycerin (96% solution) | 1.50 | 1.50 |
| Butylene Glycol | 1.00 | 1.00 |
| Tetrasodium EDTA | 0.10 | 0.10 |
| Blend (95.2% caprylyl glycol and 4.8% caprylohydroxamic acid) | — | 1.05 |
| Octinoxate | 7.50 | 7.50 |
| Oxybenzone | 5.25 | 5.25 |
| Octisalate | 5.00 | 5.00 |
| Avobenzone | 2.00 | 2.00 |
| Homosalate | 13.00 | 13.00 |
| Glyceryl Stearate and PEG-100 Stearate | 2.50 | 2.50 |
| Neopentyl Glycol Diheptanoate | 2.25 | 2.25 |
| Adipic Acid/Diethylene Glycol/Glycerin Crosspolymer | 3.00 | 3.00 |
| Hydroxyethylacrylate/Sodium Acryloyldimethyltaurate Copolymer and Squalane and Polysorbate 60 | 3.50 | 3.50 |
| Silica | 2.00 | 2.00 |
| Total | 100.00 | 100.00 |

A challenge test complying with USP and CTFA methodologies was performed. The results are in Table 2. The table indicates the log value of the number of viable organisms measured after the expired time interval. The term TNTC is the acronym for "Too Numerous To Count" and indicates that the number of viable organisms has increased as compared to the initial inoculum. Comparative Product A, containing no preservative, fails to meet the CTFA acceptance criteria of a 99% reduction in bacteria and 90% reduction in yeast and fungi within seven days. Product B, containing a preservative blend of a vicinal diol and an alkylhydroxamic acid according to the invention, meets and far exceeds the CTFA acceptance criteria.

TABLE 2

| | S. aureus | | E. coli | | P. aeruginosa | | C. albicans | | A. niger | |
|---|---|---|---|---|---|---|---|---|---|---|
| | A | B | A | B | A | B | A | B | A | B |
| Inoculum | 5.71 | 5.90 | 5.95 | 6.09 | 5.77 | 6.16 | 5.77 | 5.38 | 5.3 | 5.30 |
| Day 7 | TNTC | <1.0 | TNTC | <1.0 | TNTC | <1.0 | TNTC | <1.0 | TNTC | <1.0 |
| Day 14 | 4.41 | <1.0 | 5.17 | <1.0 | 2.53 | <1.0 | 5.03 | <1.0 | 4.9 | <1.0 |
| Day 21 | Fail | <1.0 | Fail | <1.0 | Fail | <1.0 | Fail | <1.0 | Fail | <1.0 |
| Day 28 | Fail | <1.0 | Fail | <1.0 | Fail | <1.0 | Fail | <1.0 | Fail | <1.0 |

As the results show, the compositions according to the invention hereof may be used to prepare effective preservative for personal care and pharmaceutical compositions, and contribute to preservation of topical cosmetic, toiletry and pharmaceutical compositions.

Example 2

A body wash formulation was prepared in accordance with the invention. The ingredients shown in Table 3, below, were combined to form a body wash base.

TABLE 3

| Ingredient | Amount (wt %) |
|---|---|
| Deionized water | Q.S. |
| $Na_4$ EDTA | 0.1 |
| PEG150 distearate | 0.75 |
| Sodium lauryl ether sulfate (30% soln.) | 8 |
| Lexaine C | 19.3 |

TABLE 3-continued

| Ingredient | Amount (wt %) |
|---|---|
| Lexquat C | 2 |
| PEG 80 Sorbitan laurate | 15 |
| $NaCl_2$ | 0.8 |

Three formulations (A, B, and C) were prepared using the base body wash. To formulation A was added 0.70 wt. % of a CHA blend, to formulation B was added 0.80 of a CHA blend, to formulation C was added 1.0% of a CHA blend. The CHA blend used in each case was composed of caprylohydroxamic acid, caprylyl glycol, and glycerin in a weight ratio of 15:71:14, respectively.

LEXAINE C is a proprietary formulation of cocamidylpropyl betaine. LEXQUAT C is a proprietary formulation of cocamidylpropyl PG-dimonium chloride. Both are available from Inolex Chemical Company, Philadelphia, Pa.

A preservative efficacy test ("PET") was preformed using each formulation A, B, and C. The results are shown below in Tables 4, 5, and 6.

TABLE 4

(Formulation A)
$Log_{-10}$ CFU/g

| | Staphyloccous aureus | Esherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | 4.11 | 3.53 | 2.52 | 2.20 | 4.71 |
| Day 2 | 3.18 | 3.21 | <1.00 | <1.00 | 4.02 |
| Day 7 | <1.00 | 1.78 | <1.00 | <1.00 | 3.78 |
| Day 14 | <1.00 | <1.00 | <1.00 | <1.00 | 3.47 |
| Day 21 | <1.00 | <1.00 | <1.00 | <1.00 | 3.39 |
| Day 28 | <1.00 | <1.00 | <1.00 | <1.00 | 3.40 |

TABLE 5

(Formulation B)
$Log_{-10}$ CFU/g

| | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | 4.56 | 4.45 | 2.66 | 2.16 | 4.26 |
| Day 2 | 4.01 | 3.50 | <1.00 | <1.00 | 4.96 |
| Day 7 | 1.48 | 2.16 | <1.00 | <1.00 | 2.98 |
| Day 14 | <1.00 | <1.00 | <1.00 | <1.00 | 3.48 |
| Day 21 | <1.00 | <1.00 | <1.00 | <1.00 | 3.24 |
| Day 28 | <1.00 | <1.00 | <1.00 | <1.00 | 3.28 |

TABLE 6

(Formulation C)
$Log_{10}$ CFU/g

|  | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | 4.62 | 4.41 | 2.51 | 1.18 | 4.35 |
| Day 2 | 3.43 | 3.72 | <1.00 | <1.00 | 4.90 |
| Day 7 | 1.48 | 1.79 | <1.00 | <1.00 | 3.88 |
| Day 14 | <1.00 | <1.00 | <1.00 | <1.00 | 3.59 |
| Day 21 | <1.00 | <1.00 | <1.00 | <1.00 | 3.24 |
| Day 28 | <1.00 | <1.00 | <1.00 | <1.00 | 3.31 |

Example 3

A lotion formulation was prepared in accordance with the invention. A base lotion formulation was prepared by incorporating the ingredients and amounts as shown below.

| Ingredient | Amount (wt %) |
|---|---|
| Deionized water | Q.S. |
| Keltrol CG | 0.3 |
| Glycerine | 5 |
| Sodium borate | 0.2 |
| Lexol GT-865 | 15 |
| Stearic acid | 4.5 |
| Beeswax | 4 |
| Tocopheryl acetate | 0.1 |
| Orange wax | 0.5 |
| Tegosoft PSE 141G | 2.5 |

KELTROL CG is a proprietary formulation of xanthan gum, available from CP Kelco, Atlanta, Ga. LEXOL GT 865 is a proprietary formulation of propylene glycol dicaprylate/dicaprate, available from Inolex Chemical Company, Philadelphia, Pa. TEGOSOFT PSE is a proprietary formulation of sucrose monostearate mixed with tallow alcohol/coconut alcohol available from Evonik Goldschmidt of Parsippany, N.J.

Using this base, three formulations were prepared (D, E and F). To formulation D was added contained a CHA blend in the amount of 0.7% by weight; E contained a CHA blend in an amount of 0.8% by weight, and F contains a blend on an amount of 1.0% by weight. In each instance the CHA blend consisted of caprylohydroxamic acid, caprylyl glycol, and glycerin in a weight ratio of 15:71:14, respectively.

PET evaluations were carried out on each formulation, and the results are shown below in Tables 7-9.

TABLE 7

(Formulation D)
$Log_{10}$ CFU/g

|  | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | 4.78 | 2.33 | <1.00 | 4.37 | 4.40 |
| Day 2 | 4.08 | <1.00 | <1.00 | 4.12 | 4.78 |
| Day 7 | <1.00 | <1.00 | <1.00 | <1.00 | 3.61 |
| Day 14 | <1.00 | <1.00 | <1.00 | <1.00 | 2.65 |
| Day 21 | <1.00 | <1.00 | <1.00 | <1.00 | 2.35 |
| Day 28 | <1.00 | <1.00 | <1.00 | <1.00 | 2.04 |

TABLE 8

(Formulation E)
$Log_{10}$ CFU/g

|  | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | 2.32 | <1.00 | <1.00 | 3.45 | 4.65 |
| Day 2 | <1.00 | <1.00 | <1.00 | <1.00 | 4.73 |
| Day 7 | <1.00 | <1.00 | <1.00 | <1.00 | 3.20 |
| Day 14 | <1.00 | <1.00 | <1.00 | <1.00 | <1.00 |
| Day 21 | <1.00 | <1.00 | <1.00 | <1.00 | <1.00 |
| Day 28 | <1.00 | <1.00 | <1.00 | <1.00 | <1.00 |

TABLE 9

(Formulation F)
Log$_{10}$ CFU/g

| | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | <1.00 | <1.00 | <1.00 | 2.49 | 4.45 |
| Day 2 | <1.00 | <1.00 | <1.00 | <1.00 | 4.41 |
| Day 7 | <1.00 | <1.00 | <1.00 | <1.00 | 2.60 |
| Day 14 | <1.00 | <1.00 | <1.00 | <1.00 | <1.00 |
| Day 21 | <1.00 | <1.00 | <1.00 | <1.00 | <1.00 |
| Day 28 | <1.00 | <1.00 | <1.00 | <1.00 | <1.00 |

Example 4

A sunscreen lotion base formulation having SPF 28 was prepared by incorporating the ingredients shown below in Table 10:

TABLE 10

| Ingredient | Amount (wt. %) |
|---|---|
| Deionized water | Q.S. |
| Keltrol CG | 0.4 |
| glycerin (96% solution) | 1.5 |
| Na$_4$ EDTA | 0.1 |
| butylene glycol | 1 |
| Simugel | 3.5 |
| Octinoxate | 7.5 |
| Homosalate | 13 |
| Octisalate | 5 |
| Oxybenzone | 5.25 |
| Auobenzone | 2 |
| LEXOREZ 100 | 3 |
| LEXFEEL 7 | 2.25 |
| LEXEMUL 561 | 2.5 |

SIMUGEL is a proprietary formulation of ammonium polyacrylate/isohexadane/PEG-40 available from SEPPIC, Countryside, Ill. LEXOREZ 1 is a proprietary formulation of adipic acid/diethylene glycol/glycerin, LEXFEEL 7 is a proprietary formulation of neopentyl glycol diheptanoate, and LEXEMUL 561 is a proprietary formulation of glyceryl stearate PEG-100 stearate; all are available from Inolex Chemical Company, Philadelphia, Pa.

Three formulations (G, H, I) were prepared. To formulation G was added a CHA blend in an amount of 0.7 wt %. To formulation H, was added a CHA blend in an amount of 0.8 wt %. To formulation I was added a CHA blend in an amount of 1.0% by weight. The CHA blend used in each case was composed of caprylohydroxamic acid, caprylyl glycol, and glycerin in a weight ratio of 15:71:14, respectively.

A PET evaluation was carried out on each formulation and the data/results are shown below in Tables 11, 12, and 13.

TABLE 11

(Formulation G)
Log$_{10}$ CFU/g

| | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | 4.52 | <1.00 | <1.00 | 4.27 | 4.64 |
| Day 2 | <1.00 | <1.00 | <1.00 | 1.60 | 4.24 |
| Day 7 | <1.00 | <1.00 | <1.00 | <1.00 | 1.90 |
| Day 14 | <1.00 | <1.00 | <1.00 | <1.00 | <1.00 |
| Day 21 | <1.00 | <1.00 | <1.00 | <1.00 | <1.00 |
| Day 28 | <1.00 | <1.00 | <1.00 | <1.00 | <1.00 |

TABLE 12

(Formulation H)
Log$_{10}$ CFU/g

| | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | 2.57 | <1.00 | <1.00 | 3.19 | 4.91 |
| Day 2 | <1.00 | <1.00 | <1.00 | <1.00 | 4.00 |
| Day 7 | <1.00 | <1.00 | <1.00 | <1.00 | <1.00 |
| Day 14 | <1.00 | <1.00 | <1.00 | <1.00 | <1.00 |
| Day 21 | <1.00 | <1.00 | <1.00 | <1.00 | <1.00 |
| Day 28 | <1.00 | <1.00 | <1.00 | <1.00 | <1.00 |

TABLE 13

(Formulation I)
Log$_{10}$ CFU/g

| | Staphylococcus aureus | Escherichia coli | Pseudomonas aeruginosa | Candida albicans | Aspergillus niger |
|---|---|---|---|---|---|
| Inoculum level | 5.94 | 6.13 | 5.75 | 5.56 | 5.24 |
| Day 1 | <1.00 | <1.00 | <1.00 | <1.00 | 4.49 |
| Day 2 | <1.00 | <1.00 | <1.00 | <1.00 | 4.08 |
| Day 7 | <1.00 | <1.00 | <1.00 | <1.00 | <1.00 |
| Day 14 | <1.00 | <1.00 | <1.00 | <1.00 | <1.00 |
| Day 21 | <1.00 | <1.00 | <1.00 | <1.00 | <1.00 |
| Day 28 | <1.00 | <1.00 | <1.00 | <1.00 | <1.00 |

Example 5

A base SPF 28 sunscreen lotion was prepared using by the components and amounts shown in Table 10, below. Using this base, six formulations (J1, J2, J3, K1, K2, and L) were prepared. Each formulation was prepared by using the CHA blend in the amount noted below in Table 14:

TABLE 14

| Formulation | Blend Caprylohydroxamic acid/glyceryl caprylate/ methylpropanediol (10:75:15 wt ratio) | Blend Caprylohydroxamic acid/ethylhexylglycerin/ methylpropanediol (15:30:55 wt ratio) | Blend Caprylohydroxamic acid/phenoxyethanol// methylpropanediol/ water (15:70:7.5:7.5 wt ratio) |
|---|---|---|---|
| J1 | 1.0 wt % | 0 | 0 |
| J2 | 1.2 wt % | 0 | 0 |
| J3 | 1.5 wt % | 0 | 0 |
| K1 | 0 | 1.0 wt % | 0 |
| K2 | 0 | 1.2 wt % | 0 |
| L | 0 | 0 | 1.0 wt % |

A PET evaluation was carried out and the results are shown in Tables 15-20.

TABLE 15

(Formulation J1)
Log$_{10}$ CFU/g

| | Staphylococcus aureus | Escherichia coli | Pseudomonas aeruginosa | Candida albicans | Aspergillus niger |
|---|---|---|---|---|---|
| Inoculum level | 5.86 | 6.16 | 6.03 | 5.31 | 5.17 |
| Day 1 | <1.00 | <1.00 | <1.00 | 3.74 | 4.74 |
| Day 2 | <1.00 | <1.00 | <1.00 | 2.40 | 4.61 |
| Day 7 | <1.00 | <1.00 | <1.00 | <1.00 | 3.74 |
| Day 14 | <1.00 | <1.00 | <1.00 | 1.18 | 2.44 |
| Day 21 | <1.00 | <1.00 | <1.00 | <1.00 | 2.31 |
| Day 28 | <1.00 | <1.00 | <1.00 | <1.00 | 1.00 |
| Validation | + | + | + | + | + |

TABLE 16

(Formulation J2)
Log$_{10}$ CFU/g

| | Staphylococcus aureus | Escherichia coli | Pseudomonas aeruginosa | Candida albicans | Aspergillus niger |
|---|---|---|---|---|---|
| Inoculum level | 5.86 | 6.16 | 6.03 | 5.31 | 5.17 |
| Day 1 | <1.00 | <1.00 | <1.00 | 3.22 | 4.88 |
| Day 2 | <1.00 | <1.00 | <1.00 | <1.00 | 4.60 |
| Day 7 | <1.00 | <1.00 | <1.00 | <1.00 | 3.55 |
| Day 14 | <1.00 | <1.00 | <1.00 | <1.00 | 2.04 |
| Day 21 | <1.00 | <1.00 | <1.00 | <1.00 | <1.00 |

TABLE 16-continued (Formulation J2)
$Log_{10} CFU/g$

| | Staphylococcus aureus | Escherichia coli | Pseudomonas aeruginosa | Candida albicans | Aspergillus niger |
|---|---|---|---|---|---|
| Day 28 | <1.00 | <1.00 | <1.00 | <1.00 | <1.00 |
| Validation | + | + | + | + | + |

TABLE 17

(Formulation J3)
$Log_{10} CFU/g$

| | Staphylococcus aureus | Escherichia coli | Pseudomonas aeruginosa | Candida albicans | Aspergillus niger |
|---|---|---|---|---|---|
| Inoculum level | 5.86 | 6.16 | 6.03 | 5.31 | 5.17 |
| Day 1 | <1.00 | <1.00 | <1.00 | 3.13 | 4.54 |
| Day 2 | <1.00 | <1.00 | <1.00 | <1.00 | 4.29 |
| Day 7 | <1.00 | <1.00 | <1.00 | <1.00 | 2.52 |
| Day 14 | <1.00 | <1.00 | <1.00 | <1.00 | <1.00 |
| Day 21 | <1.00 | <1.00 | <1.00 | <1.00 | <1.00 |
| Day 28 | <1.00 | <1.00 | <1.00 | <1.00 | <1.00 |
| Validation | + | + | + | + | + |

TABLE 18

(Formulation K1)
$Log_{10} CFU/g$

| | Staphylococcus aureus | Escherichia coli | Pseudomonas aeruginosa | Candida albicans | Aspergillus niger |
|---|---|---|---|---|---|
| Inoculum level | 5.86 | 6.16 | 6.03 | 5.31 | 5.17 |
| Day 1 | 2.18 | <1.00 | <1.00 | 3.13 | 4.81 |
| Day 2 | <1.00 | <1.00 | <1.00 | <1.00 | 4.60 |
| Day 7 | <1.00 | <1.00 | <1.00 | <1.00 | 3.11 |
| Day 14 | <1.00 | <1.00 | <1.00 | 1.70 | <1.00 |
| Day 21 | <1.00 | <1.00 | <1.00 | <1.00 | <1.00 |
| Day 28 | <1.00 | <1.00 | <1.00 | <1.00 | <1.00 |
| Validation | + | + | + | + | + |

TABLE 19

(Formulation K2)
$Log_{10} CFU/g$

| | Staphylococcus aureus | Escherichia coli | Pseudomonas aeruginosa | Candida albicans | Aspergillus niger |
|---|---|---|---|---|---|
| Inoculum level | 5.86 | 6.16 | 6.03 | 5.31 | 5.17 |
| Day 1 | 2.63 | <1.00 | <1.00 | 3.29 | 4.53 |
| Day 2 | <1.00 | <1.00 | <1.00 | <1.00 | 4.23 |
| Day 7 | <1.00 | <1.00 | <1.00 | <1.00 | 2.11 |
| Day 14 | <1.00 | <1.00 | <1.00 | 1.90 | <1.00 |
| Day 21 | <1.00 | <1.00 | <1.00 | <1.00 | <1.00 |
| Day 28 | <1.00 | <1.00 | <1.00 | <1.00 | <1.00 |
| Validation | + | + | + | + | + |

TABLE 20

(Formulation L)
Log-10 CFU/g

| | Staphylococcus aureus | Escherichia coli | Pseudomonas aeruginosa | Candida albicans | Aspergillus niger |
|---|---|---|---|---|---|
| Inoculum level | 5.86 | 6.16 | 6.03 | 5.31 | 5.17 |
| Day 1 | 3.37 | <1.00 | <1.00 | 3.43 | 4.45 |
| Day 2 | <1.00 | <1.00 | <1.00 | 1.65 | 4.18 |

TABLE 20-continued (Formulation L)
Log-10 CFU/g

|  | Staphylococcus aureus | Escherichia coli | Pseudomonas aeruginosa | Candida albicans | Aspergillus niger |
| --- | --- | --- | --- | --- | --- |
| Day 7 | <1.00 | <1.00 | <1.00 | <1.00 | <1.00 |
| Day 14 | <1.00 | <1.00 | <1.00 | <1.00 | <1.00 |
| Day 21 | <1.00 | <1.00 | <1.00 | <1.00 | <1.00 |
| Day 28 | <1.00 | <1.00 | <1.00 | <1.00 | <1.00 |
| Validation | + | + | + | + | + |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of preserving a topical cosmetic, toiletry or pharmaceutical formulation against microbiological growth comprising adding an effective amount of a blend consisting of at least one hydroxamic acid, or a salt and/or a complex thereof and a diol, wherein the formulation is preserved against microbiological growth over time.

2. The method according to claim 1, wherein the at least one hydroxamic acid comprises an alkylhydroxamic acid.

3. The method according to claim 1, wherein the alkylhydroxamic acid comprises a linear or branched, saturated or unsaturated, substituted or unsubstituted, carbon chain of two to about twenty-two carbon atoms.

4. The method according to claim 1, wherein the alkylhydroxamic acid comprises a linear carbon chain of about six to about twelve carbon atoms.

5. The method according to claim 1, wherein the at least one alkylhydroxamic acid is selected from the group consisting of hexanohydroxamic acid, caprylohydroxamic acid, caprohydroxamic acid, laurohydroxamic acid and mixtures and combinations thereof.

6. The method according to claim 5, wherein the alkylhydroxamic acid is caprylohydroxamic acid.

7. The method according to claim 1 wherein the at least one diol is a vicinal diol.

8. The method according to claim 7, wherein the at least one vicinal diol is a 1,2-alkanediol.

9. The method according to claim 8, wherein the at least one 1,2-alkanediol is selected from the group consisting of 1,2-pentanediol, 1,2-hexanediol, caprylyl glycol and mixtures and combinations thereof.

10. The method according to claim 7, wherein the at least one vicinal diol is a glyceryl monoester and/or a glyceryl monoether.

11. The method according to claim 10, wherein the at least one glyceryl monoester is selected from the group consisting of glyceryl monocaprate, glyceryl mono caproate, and glyceryl monocaprylate.

12. The method according to claim 7, wherein the at least one glyceryl monoether is ethylhexyl glycerine.

13. A method of preserving a topical cosmetic, toiletry or pharmaceutical formulation against microbiological growth comprising adding an effective amount of a blend consisting of at least one hydroxamic acid, or a salt and/or a complex thereof and a diol, wherein the formulation is parabens free and is preserved against microbiological growth over time.

14. The method according to claim 13, wherein the at least one hydroxamic acid comprises an alkylhydroxamic acid.

15. The method according to claim 13, wherein the alkylhydroxamic acid comprises a linear or branched, saturated or unsaturated, substituted or unsubstituted, carbon chain of two to about twenty-two carbon atoms.

16. The method according to claim 13, wherein the at least one alkylhydroxamic acid is selected from the group consisting of hexanohydroxamic acid, caprylohydroxamic acid, caprohydroxamic acid, laurohydroxamic acid and mixtures and combinations thereof.

17. The method according to claim 13, wherein the at least one diol is a vicinal diol.

18. The method according to claim 17, wherein the at least one vicinal diol is a 1,2-alkanediol.

19. A method of preserving a topical cosmetic, toiletry or pharmaceutical formulation against microbiological growth comprising adding an effective amount of a blend consisting of at least one hydroxamic acid, or a salt and/or a complex thereof, an aromatic alcohol and a diol, wherein the formulation is preserved against microbiological contamination and growth over time.

20. The method according to claim 19, wherein the at least one hydroxamic acid comprises an alkylhydroxamic acid.

21. The method according to claim 19, wherein the alkylhydroxamic acid comprises a linear or branched, saturated or unsaturated, substituted or unsubstituted, carbon chain of two to about twenty-two carbon atoms.

22. The method according to claim 19, wherein the at least one hydroxamic acid is selected from the group consisting of hexanohydroxamic acid, caprylohydroxamic acid, caprohydroxamic acid, laurohydroxamic acid and mixtures and combinations thereof.

23. The method according to claim 19, wherein the aromatic alcohol is phenoxyethanol.

* * * * *